(12) United States Patent
De Waal Malefyt et al.

(10) Patent No.: US 7,445,779 B2
(45) Date of Patent: Nov. 4, 2008

(54) METHODS OF MODULATING IFNγ PRODUCTION

(75) Inventors: Rene De Waal Malefyt, Sunnyvale, CA (US); Marilyn Travis, San Carlos, CA (US); Elena Vaisberg, Foster City, CA (US)

(73) Assignee: Schering Corporation, Kenilworth, NJ (US)

( * ) Notice: Subject to any disclaimer, the term of this patent is extended or adjusted under 35 U.S.C. 154(b) by 638 days.

(21) Appl. No.: 10/741,429

(22) Filed: Dec. 18, 2003

(65) Prior Publication Data

US 2004/0219096 A1 Nov. 4, 2004

Related U.S. Application Data

(60) Provisional application No. 60/437,515, filed on Dec. 31, 2002.

(51) Int. Cl.
*A61K 39/395* (2006.01)
*A61K 38/19* (2006.01)

(52) U.S. Cl. ................ 424/145.1; 424/143.1; 424/85.2; 514/12

(58) Field of Classification Search ........................ None
See application file for complete search history.

(56) References Cited

OTHER PUBLICATIONS

Vitetta et al. Science, Jul. 21, 2006, vol. 313, pp. 308-309.*
Immunobiology, Immune System in Health and Disease, Third Edition, Janeway and Travers, Ed., 1997.*
Biet, Franck, et al., "Mycobacterium bovis BCG Producing Interleukin-18 Increases Antigen-Specific Gamma Interferon Production in Mice", *Infection and Immunity*, 70(12):6549-6557, Dec. 2002.
Bouma, G. and Strober, W., "The Immunological and Genetic Basis of Imflammatory Bowel Disease", *Nature Reviews—Immunology*, 3:521-533, Jul. 2003.
Chen, Ling, et al., "Eradication of Murine Bladder Carcinoma by Intratumor Injection of a Bicistronic Adenoviral Vector Carrying cDNAs for the IL-12 Heterodimer and Its Inhibition by the IL-12 p40 Subunit Homodimer", *The Journal of Immunology*, 159:351-359, 1997.
Dinarello, Charles A., "Interleukin-18", *Methods*, 19:121-132, 1999.
Dorman, S. E., and Holland, S.M., "Interferon-γ and interleukin-12 pathway defects and human disease", *Cytokine & Growth Factor Reviews* 11:321-333, 2000.
Hong, Kenneth, et al., "Persistence of Pathogenic CD4$^{30}$ Th1-Like Cells In Vivo in the Absence of IL-12 but in the Presence of Autoantigen", *The Journal of Immunology*, 166:4765-4772, 2001.
Lee, Natalie C., et al., "Production of interferon-gamma by tumor-sensitized T cells is essential for interleukin-12-induced complete tumor eradication", *Surgery*, 132(2): 365-368, Aug. 2002.
Lenzi, Renato, et al., "Phase I Study of Intraperitoneal Recombinant Human Interleukin 12 in Patients with Müllerian Carcinoma, Gastrointestinal Primary Malignancies, and Mesothelioma", *Clinical Cancer Research*, 8:3686-3695, Dec. 2002.
Marshall, Jason D., et al., "The Interleukin-12-Mediated Pathway of Immune Events Is Dysfunctional in Human Immunodeficiency Virus-Infected Individuals", *Blood*, 94(3):1003-1011, Aug. 1, 1999.
Nakanishi, Kenji, et al., "Interleukin-18 is a unique cytokine that stimulates both Th1 and Th2 responses depending on its cytokine milieu", *Cytokine and Growth Factor Reviews*, 12:53-72, 2001.
Neighbors, Margaret, et al., "A Critical Role for Interleukin 18 in Primary and Memory Effector Responses to Listeria Monocytogenes that Extends Beyond its Effects on Interferon γ Production", *J. Exp. Med.*, 194(3):343-354, Aug. 6, 2001.
Oikawa, Yoichi, et al., "Systemic Administration of IL-18 Promotes Diabetes Development in Young Nonobese Diabetic Mice", *The Journal of Immunology*, 171:5865-5875, 2003.
Padigel, Udaikumar M., et al., "The Development of a Th1-Type Response and Resistance to Leishmania major Infection in the Absence of CD40-CD40L Costimulation", *The Journal of Immunology*, 167:5874-5879, 2001.
Pien, Gary C., et al., "Cutting Edge: Selective IL-18 Requirements for Induction of Compartmental IFN-γ Responses During Viral Infection", *The Journal of Immunology*, 165:4787-4791, 2000.
Pflanz, Stefan, et al., "IL-27, a Heterodimeric Cytokine Composed of EBI3 and p28 Protein, Induces Proliferation of Naïve CD4$^+$ T Cells", *Immunity*, 16:779-790, Jun. 2002.
Nieuwenhuis, Edward E. S., et al., "Disruption of T helper 2-immune responses in Epstein-Barr virus-induced gene 3-deficient mice", *PNAS*, 99(26):16951-16956, Dec. 24, 2002.
Riffault, S. et al., "Transient IFN-γ in the lymph node draining a dermal site loaded with UV-irradiated herpes simplex virus type 1: an NK- and CD3-dependent process regulated by IL-12 but not by IFN-αIβ", *Journal of General Virology*, 81:2365-2373, 2000.
Robinson, Douglas S., et al., "Further Checkpoints in Th1 Development", *Immunity*, 16:755-758, Jun. 2002.
Rönnblom, L. and Alm, G., "The Natural Interferon-α Producing Cells in Systemic Lupus Erythematosus", *Human Immunology*, 63:1181-1193, 2002.
Steinman, Lawrence, "Immunotherapy of multiple sclerosis: the end of the beginning", *Current Opinion in Immunology*, 13:597-600, 2001.
Tannenbaum, C. and Hamilton, T., "Immune-inflammatory mechanisms in IFNγ-mediated anti-tumor activity", *Cancer Biology*, 10:113-123, 2000.
Varga, Eva Maria, et al., "T Cells from Human Allergen-Induced Last Asthmatic Responses Express IL-12 Receptor βSubunit mRNA and Respond to IL-12 In Vitro", *The Journal of Immunology*, 165:2877-2885, 2000.
Wei, Xiao-qing, et al., "Reduced incidence and Severity of Collagen-Induced Arthritis in Mice Lacking IL-18", *The Journal of Immunology*, 166:517-521, 2001.

* cited by examiner

*Primary Examiner*—Bridget E. Bunner
*Assistant Examiner*—Fozia M Hamud

(57) ABSTRACT

Provided are cytokines and methods of modulating activity of the immune system using cytokine agonists and antagonists. Also provided are methods of treatment of immune and proliferative disorders.

7 Claims, No Drawings

METHODS OF MODULATING IFNγ PRODUCTION

This application claims benefit of U.S. Provisional patent application Ser. No. 60/437,515, filed Dec. 31, 2002.

FIELD OF THE INVENTION

The present invention provides methods of enhancing or inhibiting IFNgamma production in the treatment of various immune disorders.

BACKGROUND OF THE INVENTION

The mammalian immune response is based on a series of complex cellular interactions, called the "immune network". Recent research has provided new insights into the inner workings of this network. While it remains clear that much of the response does, in fact, revolve around the network-like interactions of lymphocytes, macrophages, granulocytes, and other cells, immunologists now generally hold the opinion that soluble proteins, known as cytokines play a critical role in controlling these cellular interactions. Thus, there is considerable interest in the isolation, characterization, and mechanisms of action of cell modulatory factors, an understanding of which will lead to significant advancements in the diagnosis and therapy of numerous medical abnormalities, e.g., immune system disorders. Some of these factors are hematopoietic growth and/or differentiation factors, e.g., stem cell factor (SCF) or IL-12 (see, e.g., Mire-Sluis and Thorpe (1998) *Cytokines*, Academic Press, San Diego, Calif.; Thomson (ed.) (1998)*The Cytokine Handbook* (3d ed.) Academic Press, San Diego, Calif.; Metcalf and Nicola (1995) *The Hematopoietic Colony Stimulating Factors*, Cambridge Univ. Press, Cambridge, UK; and Aggarwal and Gutterman (1991) *Human Cytokines*, Blackwell, Malden, Mass.).

Cytokines mediate cellular activities in a variety of ways. They have been shown to support the proliferation, growth, and differentiation of pluripotential hematopoietic stem cells into large numbers of progenitors comprising diverse cellular lineages making up a complex immune system. Proper and balanced interactions between the cellular components are necessary for a healthy immune response. The different cellular lineages often respond in a different manner when cytokines are administered in conjunction with other agents.

Cell lineages especially important to the immune response include: B-cells, which can produce and secrete immunoglobulins (proteins with the capability of recognizing and binding to foreign matter to effect its removal), T-cells of various subsets that secrete cytokines and induce or suppress the B-cells and various other cells (including other T-cells) making up the immune network, NK cells, which are responsible for cytokine production in response to infectious agents and tumor cells, and antigen presenting cells such as dendritic and other myeloid derived cells.

The present invention provides methods of using IL-27, a cytokine related to IL-12. IL-12 plays a critical role in cell-mediated immunity. Its activities are triggered through a high-affinity receptor complex comprising two subunits, IL-12Rbeta1 and IL-12Rbeta2. The p35 subunit of IL-12 can bind to a second soluble protein called EBI3, and it was suggested that p35 and EBI3 form a secreted heterodimer, though the function of this heterodimer is unclear. EBI3 also binds to another protein, p28, to form a soluble heterodimer comprising p28 and EBI3, now called IL-27. The p28 subunit is also known as IL-80 or IL-D80. A cDNA encoding the human and mouse p35 subunit has been described in US20020164609 and WO 02/068596, both of which are incorporated by reference (see, e.g., Devergne, et al. (1997) *Proc. Natl. Acad. Sci. USA* 94:12041-12046; Chua, et al. (1995) *J. Immunol.* 155:4286:4294; Presky, et al. (1998) *J. Immunol.* 160:2174-2179; Gately, et al. (1998) *Ann. Rev. Immunol.* 16:495-521; Presky, et al. (1996) *Proc. Natl. Acad. Sci. USA* 93:14002-14007; Trinchieri (1998) *Adv. Immunol.* 70:83-243; Trinchieri (1998) *Immunol. Res.* 17:269-278; Trinchieri (1995) *Annu. Rev. Immunol.* 13:251-276).

The present invention provides methods to modulate expression of interferon-gamma (IFNgamma) for the purpose of stimulating immune defense against bacteria and parasites, e.g., intracellular bacteria and parasites, and against viruses, cancers, and tumors. IFNgamma can mediate immune response against intracellular bacteria, where common intracellular bacterial species include *Salmonella* sp., *Shigella* sp., *Listeria* sp., *Francisella* sp., *Mycobacteria* sp. (tuberculosis; leprosy), *Legionella* sp., *Rickettsia* sp., *Orienta* sp., *Ehrlichia* sp., *Anaplasma* sp., *Neorickettsia* sp., *Chlamydia* sp., and *Coxiella* sp. Additionally, IFNgamma mediates response to parasites, e.g., *Plasmodia* sp. (malaria), *Toxoplasma* sp., *Leishmania* sp., *Trypanosonia* sp., and *Cryptosporidium* sp. Moreover, IFNgamma mediates immune defense against viruses, e.g., HIV, orthopoxviruses, such as variola virus and vaccinia virus (smallpox), and herpesviruses, including alphaherpesviruses, e.g., Herpes Simplex virus, and betaherpesviruses, e.g., *Cytomegalovirus*. Also provided are methods of reducing or inhibiting IFNgamma expression, e.g., for the treatment of chronic inflammatory disorders, such as Crohn's disease (see, e.g., Kent, et al. (2000) *Vaccine* 18:2250-2256; Ismail, et al. (2002) *FEMS Microbiol. Lett.* 207:111-120; Kaufmann (2001) *Nature Revs. Immunol.* 1:20-30; Goebel and Gross (2001) *TRENDS Microbiol.* 9:267-273; Heussler, et al. (2001) *Int. J. Parasitol.* 31:1166-1176; Luder, et al. (2001) Carsten, et al. (2001) *TRENDS Parasitol.* 17:480-486; Rook, et al. (2001) *Eur. Resp. J.* 17:537-557; Stenger and Rollinghoff (2001) *Ann. Rheum. Dis.* 60:iii43-iii46; Haas, et al. (2002) *Am. J. Dermatopathol.* 24:319-323; Dorman and Holland (2000) *Cytokine Growth Factor Revs.* 11:321-333; Smith, et al. (2002) *J. Gen. Virol.* 83 (Pt. 12) 2915-2931; Cohrs and Gilden (2001) *Brain Pathol.* 11:465-474; Tannenbaum and Hamilton (2002) *Sem. Cancer Biol.* 10:113-123; Ikeda, et al. (2002) *Cytokine Growth Factor Revs.* 13:95-109; Klimp, et al. (2002) *Crit. Rev. Oncol. Hematol.* 44:143-161; Frucht, et al. (2001) *TRENDS Immunol.* 22:556-560).

From the foregoing, it is evident that discoveries of new functions and methods relating to cytokines and cytokine receptors, e.g., relating to IL-27, IL-12, and their receptors, can contribute to new therapies for a wide range of degenerative or abnormal conditions, e.g., infections and cancers, where the therapies directly or indirectly involve the immune system and/or hematopoietic cells. In particular, the discovery and development of cytokines which enhance or potentiate the beneficial activities of known cytokines would be highly advantageous. The present invention provides methods of enhancing IFNgamma production using IL-27.

SUMMARY OF THE INVENTION

The present invention is based, in part, upon the discovery that IL-27 enhances production of interferon-gamma (IFNgamma).

The present invention provides a method of modulating interferon-gamma (IFNgamma) expression or levels or production by a cell comprising treating the cell with an effective amount of an agonist or antagonist of the cytokine IL-27. Also provided is the above method wherein the modulating is increasing and the treating is with an agonist of IL-27; or decreasing and the treating is with an antagonist of IL-27; the above method wherein the agonist is an IL-27 variant or derivative, and the IL-27 variant or derivative possesses at least one IL-27 biological property; as well as the above method wherein the IL-27 variant or derivative comprises an IL-27 hyperkine and, in addition, the above method wherein the increasing is about two-fold, about 5-fold, about 10-fold, about 20-fold, or about 50-fold greater than the expression or production level in the absence of the effective amount of IL-27, or IL-27 variant or derivative.

In another aspect, the invention provides the above method wherein the treating with an agonist further comprises treating with an agonist of IL-12 and an agonist of an additional cytokine; or the treating with an antagonist further comprises treating with an antagonist of IL-12 and an antagonist of an additional cytokine; as well as the above method wherein the additional cytokine is IL-2; IL-15; IL-23; or IL-18.

Another embodiment of the invention embraces the above method wherein the treating with an agonist further comprises treating with an agonist of two additional cytokines; or the treating with an antagonist further comprises treating with an antagonist of two additional cytokines; as well as the above method wherein the two additional cytokines are IL-2 and IL-15; IL-2 and IL-23; IL-15 and IL-23; or IL-18 and IL-2, IL-15, or IL-23.

In yet another aspect, the invention provides the above method wherein the agonist treated cell is treated with agonists of three additional cytokines; or the antagonist treated cell is treated with antagonists of three additional cytokines; as well as the above method wherein the three additional cytokines are IL-18 and IL-2 and IL-15; or IL-18 and IL-12 and IL-23.

In another embodiment, the invention provides the above method wherein the cell is a T cell; or NK cell; the above method wherein the cell is located in a subject, and the IL-27 agonist or IL-27 antagonist is administered to the subject; and the above method wherein the subject has, or is suspected of having, a disorder or pathological condition that can be treated or ameliorated by modulating IFNgamma levels in the subject.

Yet another aspect of the invention provides the above method wherein the treating is with an agonist or antagonist of IL-27 and the disorder or condition comprises cancer, neoplasm, or tumor; an intracellular pathogen; or an inflammatory or autoimmune condition; the above method wherein the treating is with an agonist or antagonist of IL-27 and the intracellular pathogen comprises *Leishmania* sp.; *Mycobacterium* sp.; *Listeria* sp.; *Toxoplasma* sp.; herpesvirus; cytomegalovirus; or human immunodeficiency virus (HIV); the above method wherein the treating is with an agonist or antagonist of IL-27 and the inflammatory or autoimmune condition comprises rheumatoid arthritis; or asthma or allergy; as well as the above method wherein the treating is with an antagonist or antagonist of IL-27 and the disorder or condition comprises a TH1 condition or disorder; multiple sclerosis; psoriasis; Crohn's disease; type I diabetes; or systemic lupus erythematosus.

The present invention also provides a method of treating or ameliorating a disorder or pathological condition of a subject by modulating expression or levels or production of IFNgamma in the subject, comprising administering an effective amount of an agonist or antagonist of the cytokine IL-27. Also provided is the above method wherein the subject is a human subject; or veterinary subject; as well as the above method wherein the modulating is increasing and the treating is with an agonist of IL-27; or decreasing and the treating is with an antagonist of IL-27 and, in addition, the above method wherein the agonist is an IL-27 variant or derivative, and the IL-27 variant or derivative possesses at least one IL-27 biological property; and the above method wherein the IL-27 variant or derivative comprises an IL-27 hyperkine, as well as the above method wherein the increasing is about two-fold, about 5-fold, about 10-fold, about 20-fold, or about 50-fold greater than the expression or production level in the absence of the administered effective amount of the IL-27, or IL-27 variant or derivative.

Moreover, the present invention also provides a method of treating or ameliorating a disorder or pathological condition of a subject by modulating expression or levels or production of IFNgamma in the subject, comprising administering an effective amount of an agonist or antagonist of the cytokine IL-27; wherein the agonist treated subject is treated with an agonist of IL-12 and an agonist of one additional cytokine; or the antagonist treated subject is treated with an antagonist of IL-12 and an antagonist of one additional cytokine. Also provided is the above method wherein the additional cytokine is IL-2; IL-15; IL-23; or IL-18; as well as the above method wherein the agonist treated subject is treated with agonists of two additional cytokines; or the antagonist treated subject is treated with antagonists of two additional cytokines; and the above method wherein the two additional cytokines are IL-2 and IL-15; IL-2 and IL-23; IL-15 and IL-23; or IL-18 and IL-2, IL-15, or IL-23.

Yet another embodiment of the invention provides the above method wherein the agonist treated subject is treated with agonists of three additional cytokines; or the antagonist treated subject is treated with antagonists of three additional cytokines; the above method wherein the three additional cytokines are IL-18 and IL-2 or IL-15; and IL-12 or IL-23; and the above method wherein the subject has, or is suspected of having, a disorder or condition that can be treated or ameliorated by modulating levels of IFNgamma in the subject and, in addition, the above method wherein the treating is with an agonist or antagonist of IL-27 and the disorder or condition comprises cancer, neoplasm, or tumor; an intracellular pathogen; or an inflammatory or autoimmune condition.

Moreover, the present invention provides the above method wherein the treating is with an agonist or antagonist of IL-27 and the intracellular pathogen comprises *Leishmania* sp.; *Mycobacterium* sp.; *Listeria* sp.; *Toxoplasma* sp.; herpesvirus; cytomegalovirus; or human immunodeficiency virus (HIV); the above method wherein the treating is with an agonist or antagonist of IL-27 and the inflammatory or autoimmune condition comprises rheumatoid arthritis; or asthma or allergy; as well as the above method wherein the treating is with an antagonist or agonist of IL-27 and the inflammatory or autoimmune condition comprises a TH1 condition or disorder; multiple sclerosis; psoriasis; Crohn's disease; type I diabetes; or systemic lupus erythematosus; and the above method wherein wherein the antagonist is derived from the antigen binding site of an antibody; or a nucleic acid.

The present invention provides the above method wherein the two additional cytokines are IL-2 and IL-12, IL-15, IL-18, or IL-23; IL-12 and IL-2, IL-15, IL-18, or IL-23; IL-15 and IL-2, IL-12, IL-18, or IL-23; IL-18 and IL-2, IL-12, IL-15, or IL-23; and IL-23 and IL-2, IL-12, IL-15, or IL-18. Also provided is the above method wherein the three additional cytokines are interleukins 2, 12, and 15; interleukins 2, 12, and 18; interleukins 2, 12, and 23; interleukins 2, 15, and 18; interleukins 2, 15, and 23; interleukins 2, 18, and 23; interleukins 12, 15, and 18; interleukins 12, 15, and 23; interleukins 12, 18, and interleukins 23; 15, 18, and 23.

DETAILED DESCRIPTION OF THE PREFERRED EMBODIMENTS

All references cited herein are incorporated herein by reference to the same extent as if each individual publication or patent application was specifically and individually indicated to be incorporated by reference.

As used herein, including the appended claims, the singular forms of words such as "a," "an," and "the," include their corresponding plural references unless the context clearly dictates otherwise.

I. Definitions.

A particularly useful application of IL-27 involves the ability of IL-27 to enhance IFNgamma production. Prior to describing this aspect of the present invention in detail, the following terms are defined. When used herein, these terms have the following meanings unless otherwise indicated.

A molecule possesses at least one "IL-27 biological activity" or "IL-27 agonist activity" if the molecule can be recognized by an antibody raised against a native IL-27 protein; or if the molecule possesses any stimulatory, inhibitory or binding activity of a native IL-27 protein. For example, the molecule may enhance an immune cell to produce IFNgamma or the molecule may bind to an IL-27 receptor. The molecule preferably binds to WSX-1/TCCR, and more preferably is capable of enhancing IFNgamma production.

"Administration" and "treatment," as it applies to a human, veterinary, animal, experimental subject, cell, tissue, organ, or biological fluid, refers to contact of an exogenous pharmaceutical, therapeutic, diagnostic agent, or composition to the animal, human, subject, cell, tissue, organ, or biological fluid. "Administration" and "treatment" can refer, e.g., to therapeutic, pharmacokinetic, diagnostic, research, and experimental methods. Treatment of a cell encompasses contact of a reagent to the cell, as well as contact of a reagent to a fluid, where the fluid is in contact with the cell. Treatment of a cell includes situations where the reagent contacts a biological fluid in a human or animal, but where the reagent has not been demonstrated to contact the cell. Treatment further encompasses situations where an administered reagent or cell is modified by metabolism, degradation, or by conditions of storage. "

"Enhancing" IFNgamma production by a cell refers to increasing the level of IFNgamma produced by the cell. The level of IFNgamma can be determined by any method established in the art, such as ELISA or cell proliferation assay. Enhancing IFNgamma production by 5 fold means that the new, increased level of IFNgamma is 5 times that of the original IFNgamma level. Similarly, enhancing IFNgamma production by 10 fold means that the increased level of IFNgamma is 10 times that of the original IFNgamma level, and so on.

Methods of using conservatively modified variants, derivatives, and muteins of polypeptides and nucleic acids of IL-27 are provided. "Conservatively modified variants" applies to both amino acid and nucleic acid sequences. With respect to particular nucleic acid sequences, conservatively modified variants refers to those nucleic acids which encode identical or essentially identical amino acid sequences or, where the nucleic acid does not encode an amino acid sequence, to essentially identical nucleic acid sequences. Because of the degeneracy of the genetic code, a large number of functionally identical nucleic acids may encode any given protein.

As to amino acid sequences, one of skill will recognize that an individual substitution to a nucleic acid, peptide, polypeptide, or protein sequence which substitutes an amino acid or a small percentage of amino acids in the encoded sequence for a conserved amino acid is a "conservatively modified variant." Conservative substitution tables providing functionally similar amino acids are well known in the art. An example of a conservative substitution is the exchange of an amino acid in one of the following groups for another amino acid of the same group (U.S. Pat. No. 5,767,063 issued to Lee, et al.; Kyte and Doolittle (1982) *J. Mol. Biol.* 157: 105-132):

(1) Hydrophobic: Norleucine, Ile, Val, Leu, Phe, Cys, or Met;
(2) Neutral hydrophilic: Cys, Ser, Thr;
(3) Acidic: Asp, Glu;
(4) Basic: Asn, Gln, His, Lys, Arg;
(5) Residues that influence chain orientation: Gly, Pro;
(6) Aromatic: Trp, Tyr, Phe;
(7) Small amino acids: Gly, Ala, Ser.

An "effective amount" is an amount of a therapeutic agent sufficient to achieve the intended purpose. For example, an effective amount of a composition for a method of enhancing IFNgamma production is an amount of the composition sufficient to result in increased IFNgamma production as compared to the level of production absent the composition. An effective amount for treating or ameliorating a disorder, disease, or medical condition is an amount sufficient to result in a reduction or complete removal of the symptoms of the disorder, disease, or medical condition. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

"Exposing" a cell to a substance refers to providing the substance to the cell directly or indirectly. The substance can be provided indirectly, for example, by providing a precursor of the substance, which is known to be converted to the substance. For instance, exposing a target cell to IL-27 can be achieved by providing to the target cell a composition comprising the IL-27 protein, or by introducing the gene(s) coding for IL-27 into the target cell. Alternatively, it can also be achieved by introducing the gene(s) coding for IL-27 into a second cell and mixing the target cell with the second cell.

"Expression" encompasses the biosynthesis of a nucleic acid, e.g., mRNA, or of a polypeptide, as well as changes in the compartmentalization of a macromolecule, e.g., by traversal from the nucleus to the cytosol, insertion into the plasma membrane, degranulation, or secretion. Expression or production of a macromolecule by the cell may include only the amount found in the cell, e.g., in a cell homogenate, at a given point in time. Generally, this definition applies to expression of non-secreted molecules. Alternatively, expression or production of a macromolecule by a cell includes the amount found in the cell plus the amount secreted and accumulated, e.g., in a cell medium or biological compartment. Generally, this definition applies to secreted or degranulated proteins, e.g., cytokines. "Levels" refers to concentrations in a compartment, including a biological compartment, e.g., in a predetermined volume of, e.g., plasma, serum, blood, interstitial fluid, cerebrospinal fluid, or urine, in a whole organ or fragment of the organ, in a compartment within an organ, e.g., red pulp, white pulp, or pancreatic islets, or in a specific cell or group of cells, e.g., macrophages.

A "hyperkine" is an engineered heterodimeric, homodimeric, or multimeric cytokine wherein at least two cytokine polypeptide subunits of the cytokine are covalently linked together (Pflanz, et al. (2002) *Immunity* 16:779-790).

An "immune cell" is a cell of the immune system, such as B cell, T cell, NK cell, monocyte, macrophage, mast cell, eosinophil, or antigen presenting cell (APC), or dendritic cell. Depending on the context, an immune cell can also be any cell that expresses mediators of immunity, an epithelial cell that expresses cytokines, depending on the context.

"Intracellular microorganism" encompasses a unicellular or multicellular organism that occupies a living cell, e.g., a host living cell, during part or all of its life cycle.

An "autoimmune" disorder, medical condition, or disease is characterized by recognition of a self antigen by a person or animal's own immune system. Autoimmune diseases include, without being limited to, multiple sclerosis, psoriasis, Graves' disease, insulin-dependent Type I diabetes, pernicious anemia, rhemumatoid arthritis, thyroiditis, glomerulonephritis, lupus erythematosus, Sjogren's syndrome, Addison's disease, chronic active hepatitis, myasthenia gravis, polymyositis/dermatomyositis, primary biliary cirrhosis, scleroderma, uveitis and vitiligo.

An human or animal subject "suspected of having" a disorder, disease, or medical condition is one that is not yet diagnosed as having the disorder, disease, or medical condition, but that shows one or more symptoms of the disorder, has a genetic disposition for the disorder, or has been previously treated for disorder, where the disorder is subject to recurrence.

A "neoplasm" or "tumor" is an abnormal tissue growth, generally forming a distinct mass, that grows by cellular proliferation more rapidly than normal tissue growth. Neoplasms may show partial or total lack of structural organization and functional coordination with normal tissue. As used herein, a neoplasm is intended to encompass hematopoietic neoplasms as well as solid neoplasms. A neoplasm may be benign (benign tumor) or malignant (malignant tumor or cancer). Malignant tumors can be broadly classified into three major types. Malignant neoplasms arising from epithelial structures are called carcinomas, malignant neoplasms that originate from connective tissues such as muscle, cartilage, fat or bone are called sarcomas and malignant tumors affecting hematopoietic structures (structures pertaining to the formation of blood cells) including components of the immune system, are called leukemias and lymphomas. Other neoplasms include, but are not limited to neurofibromatosis.

"Nucleic acid" encompasses single stranded nucleic acids as well as double stranded nucleic acids comprised of a complex of a single stranded nucleic acid strand and its complementary strand. The present invention encompasses methods of using a nucleic acid, e.g., residing in an expression vector, comprising a nucleic acid encoding IL-27 only; IL-2 only; IL-12 only; IL-15 only; IL-18 only; IL-23 only; IL-27 and IL-2; IL-27 and IL-15; IL-27 and IL-12; IL-27 and IL-23; IL-27 and IL-18; IL-27, IL-2 and IL-18; IL-27, IL-15 and IL-18; IL-27, IL-12 and IL-18; as well as IL-27, IL-23, and IL-18. The invention also provides a method of using the above nucleic acid, where the nucleic acid also encodes one or more of IL-1, IL-12, IL-15, IL-18, or IL-23. Also encompassed are methods of using a nucleic acid encoding all the above cytokines.

The invention contemplates methods where, e.g., all the above nucleic acids are encoded by one vector; where one nucleic acid is encoded by a first vector and where the remaining nucleic acids are encoded by a second vector; and where each nucleic acid is encoded by separate, respective vectors, and various combinations thereof. Also contemplated are methods that provide the above cytokines, where one or more cytokines are provided by a vector and where one or more cytokines are directly provided by a cytokine polypeptide, e.g., treatment with a composition comprising a vector and a polypeptide. The vectors of the contemplated method comprise, e.g., a first promoter operably linked with a first nucleic acid; a second promoter operably linked with a second nucleic acid; a third promoter operably linked with a third nucleic acid, and the like, as well as a first promoter operably linked with a first and second nucleic acid, a first promoter operably linked with a first, second, and third nucleic acid, and the like.

"Treating or ameliorating" means the reduction or complete removal of the symptoms of a disorder, disease, or medical condition.

II. General.

The present invention provides a method of enhancing IFNgamma production from an immune cell by using IL-27. Thus, as disclosed below, T cells and NK cells can be stimulated to produce IFNgamma by cytokines. It has been shown previously that IL-2, IL-12, IL-15, IL-18 and IL-23 are the most effective in stimulating IFNgamma production, alone or in combination. When the cell is also exposed to IL-27, the production of IFNgamma is synergistically enhanced, up to 100 fold compared to the production level absent IL-27. Therefore, the present invention provides a method of effectively producing IFNgamma.

This method can be applied in vitro or in vivo. To facilitate in vitro production of IFNgamma, IL-27 can be added to immune cell cultures to increase the yield of IFNgamma. Preferably, at least one additional cytokine is also added to the culture, in particular IL-2, IL-12, IL-15, IL-18 and/or IL-23. The cytokines are preferably a combination of IL-2 (or IL-15) with IL-12 (or IL-23 or IL-18), in addition to IL-27. IL-27 can be added to the combination of IL-2 (or IL-15), IL-12 (or IL-23) and IL-18. In response to IL-27, IFNgamma production is expected to increase several fold over the level of IFNgamma without IL-27, preferably by at least about 5, 10, 15, 20, 50, 75, 100, 200, 500, 750 or 1000 fold.

The invention provides methods of treating cells, ex vivo, with IL-27, or with IL-27 and one, two, three, or more cytokines, followed by introduction of the treated cells into a subject. For example, the cell(s) can be treated ex vivo with IL-27, IL-2, IL-12, and IL-18, followed by introduction of the cell(s) into a human or animal subject.

The invention also provides methods wherein the cell is treated ex vivo with one, two, three, or more cytokines, and wherein the subject is treated with the same or different one, two, three, or more cytokines. For example, the invention provides a method where the cell is treated ex vivo with IL-27 and IL-2, and where the subject is treated with IL-18. Alternatively, e.g., the cell is treated ex vivo with IL-18, and the subject is treated with IL-27 and IL-2.

The method can also be used to enhance IFNgamma production in an animal, particularly a mammal, e.g., a human, monkey, ape, rodent, or agricultural mammal, or veterinary subject. Thus, IL-27 can be administered to an animal by any method known in the art, e.g., by intravenous, subcutaneous, intramuscular, cerebral, dermal, ocular, rectal, or viral vector methods. Preferably, IL-27 is administered in a pharmaceutical composition that also comprises at least one additional cytokine and a pharmaceutically acceptable excipient/carrier. The additional cytokine is preferably IL-2, IL-12, IL-15, IL-18 and/or IL-23, more preferably a combination of IL-2 (or IL-15) with IL-12 (or IL-23 or IL-18), and most preferably a combination of IL-2 (or IL-15), IL-12 (or IL-23) and IL-18. The composition preferably enhances the blood IFNgamma level of the animal by at least about 5, 10, 15, 20, 50, 75, 100, 200, 500, 750 or 1000 folds.

IFNgamma is the principal macrophage-activating cytokine and serves critical functions in innate immunity as well as specific cell-mediated immunity. By releasing IFNgamma, T cells and NK cells activate macrophages to kill phagocytosed microorganisms. Therefore, IFNgamma plays an important role in the defense against microbial infections, particularly infections by intracellular microorganisms. IFNgamma also increases class I MHC expression on neoplastic cells, thus increasing sensitivity of the neoplastic cells to lysis by cytotoxic T cells. Moreover, IFNgamma is the signature cytokine of the Th1 subset of helper T cells, resulting in a Th1 response rather than a Th 2 response, thereby inhibiting IgE-dependent allergic reactions.

The study of the present invention has shown that IL-27 enhances IFNgamma production, and it is known that disruption of WSX-1/TCCR, a receptor for IL-27, leads to lowered expression of IFNgamma. Therefore, an antagonist of IL-27 can be used to reduce IFNgamma production in vivo or in vitro. The antagonist can be an antibody, or a fragment thereof, against IL-27, p28, or EBI3. Moreover antagonist can comprise a structural variant or mutein of IL-27, or a variant or mutein of an IL-27 receptor, e.g., a soluble receptor, that is capable of reducing IFNgamma expression.

The antagonist can also be an antisense nucleic acid that is complementary to an IL-27 mRNA (namely the mRNA for p28 or EBI3), or that is complementary to an IL-27R mRNA, or an interference RNA nucleic acid.

The present invention further provides a method of screening for IL-27 agonists or antagonists. Antagonists can be screened based on the ability to inhibit the activity of IL-27 to enhance IFNgamma production. For example, an assay system can be established wherein NK cells are contacted with IL-27 to increase IFNgamma production level. A test compound is then added to the assay and IFNgamma level measured. The test compounds that abolish the effect of IL-27 in IFNgamma production without affecting the baseline IFNgamma production in the absence of IL-27 are likely to be specific IL-27 antagonists. Similarly, the ability of IL-27 to enhance IFNgamma production can be used in an assay system for IL-27 agonists.

III. Antagonists and Agonists.

Blockage of the activities of IL-27 can be achieved by an IL-27 antagonist, e.g., an antibody to the ligand, IL-27, an antibody to a subunit of the ligand, e.g., anti-p28 antibody or anti-EBI3 antibody, an antibody that binds to both p28 and EBI3, an antibody to the receptor, e.g., WSX-1, or a soluble WSX-1, receptor protein. Interference with the ligand-receptor interaction has proven to be an effective strategy for the development of antagonists.

There are various methods to antagonize the activity mediated by ligand, e.g., to block the ligand with an antibody or to block the receptor with an antibody. Various epitopes will exist on each which will block their interaction, e.g., causing steric hindrance blocking interaction. The ability of an antibody to bind to a ligand, or to bind to a receptor, does not necessarily mean that the antibody will also block signaling, i.e., the antibody's may have no detectable effect on signaling, or the antibody may be an agonistic antibody. Another method is to use a ligand mutein or variant which retains receptor binding activity, but fails to induce receptor signaling. The mutein may be a competitive inhibitor of signaling ligand.

Alternatively, small molecule libraries may be screened for compounds which may block the interaction or signaling mediated by an identified ligand-receptor pairing.

The present invention provides for the use of an antibody or binding composition which specifically binds to a specified cytokine ligand, preferably mammalian, e.g., primate, human, cat, dog, rat, or mouse. Antibodies can be raised to various cytokine proteins, including individual, polymorphic, allelic, strain, or species variants, and fragments thereof, both in their naturally occurring (full-length) forms or in their recombinant forms. Additionally, antibodies can be raised to receptor proteins in both their native (or active) forms or in their inactive, e.g., denatured, forms. Anti-idiotypic antibodies may also be used.

A number of immunogens may be selected to produce antibodies specifically reactive with ligand or receptor proteins. Recombinant protein is a preferred immunogen for the production of monoclonal or polyclonal antibodies. Naturally occurring protein, from appropriate sources, e.g., primate, rodent, etc., may also be used either in pure or impure form. Synthetic peptides, made using the appropriate protein sequences, may also be used as an immunogen for the production of antibodies. Recombinant protein can be expressed and purified in eukaryotic or prokaryotic cells as described, e.g., in Coligan, et al. (eds.) (1995 and periodic supplements) *Current Protocols in Protein Science*, John Wiley & Sons, New York, N.Y.; and Ausubel, et al (eds.) (1987 and periodic supplements) *Current Protocols in Molecular Biology*, Greene/Wiley, New York, N.Y. Naturally folded or denatured material can be used, as appropriate, for producing antibodies. Either monoclonal or polyclonal antibodies may be generated, e.g., for subsequent use in immunoassays to measure the protein, or for immunopurification methods.

Methods of producing polyclonal antibodies are well known to those of skill in the art. Typically, an immunogen, preferably a purified protein, is mixed with an adjuvant and animals are immunized with the mixture. The animal's immune response to the immunogen preparation is monitored by taking test bleeds and determining the titer of reactivity to the protein of interest. For example, when appropriately high titers of antibody to the immunogen are obtained, usually after repeated immunizations, blood is collected from the animal and antisera are prepared. Further fractionation of the antisera to enrich for antibodies reactive to the protein can be performed if desired. See, e.g., Harlow and Lane; or Coligan. Immunization can also be performed through other methods, e.g., DNA vector immunization. See, e.g., Wang, et al. (1997) *Virology* 228:278-284.

Monoclonal antibodies may be obtained by various techniques familiar to researchers skilled in the art. Typically, spleen cells from an animal immunized with a desired antigen are immortalized, commonly by fusion with a myeloma cell. See, Kohler and Milstein (1976) *Eur. J. Immunol.* 6:511-519. Alternative methods of immortalization include transformation with Epstein Barr Virus, oncogenes, or retroviruses, or other methods known in the art. See, e.g., Doyle, et al. (eds.) (1994 and periodic supplements) *Cell and Tissue Culture. Laboratory Procedures*, John Wiley and Sons, New York, N.Y. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according, e.g., to the general protocol outlined by Huse, et al. (1989) *Science* 246:1275-1281.

Antibodies or binding compositions, including binding fragments and single chain versions, against predetermined fragments of ligand or receptor proteins can be raised by immunization of animals with conjugates of the fragments with carrier proteins. Monoclonal antibodies are prepared from cells secreting the desired antibody. These antibodies can be screened for binding to normal or defective protein. Antibodies or binding compositions will usually bind with at least a $K_D$ of about $10^{-3}$ M, more usually at least $10^{-6}$ M, typically at least $10^{-7}$ M, more typically at least $10^{-8}$ M, preferably at least about $10^{-9}$ M, and more preferably at least $10^{-10}$ M, and most preferably at least $10^{-11}$ M (see, e.g., Presta, et al. (2001) Thromb. Haemost. 85:379-389; Yang, et al. (2001) Crit. Rev. Oncol. Hematol. 38:17-23; Carnahan, et al. (2003) Clin. Cancer Res. (Suppl.) 9:3982s-3990s).

In some instances, it is desirable to prepare monoclonal antibodies (mAbs) from various mammalian hosts, such as mice, rodents, primates, humans, etc. Description of techniques for preparing such monoclonal antibodies may be found in, e.g., Stites, et al. (eds.) Basic and Clinical Immunology (4th ed.) Lange Medical Publications, Los Altos, Calif., and references cited therein; Harlow and Lane (1988) Antibodies: A Laboratory Manual, CSH Press; Goding (1986) Monoclonal Antibodies. Principles and Practice (2d ed.) Academic Press, New York, N.Y.; and particularly in Kohler and Milstein (1975) Nature 256:495-497, which discusses one method of generating monoclonal antibodies. Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see, Cabilly, U.S. Pat. No. 4,816,567; and Queen, et al. (1989) Proc. Natl. Acad. Sci. USA 86:10029-10033; or made in transgenic mice, see Mendez, et al. (1997) Nature Genetics 15:146-156; also see Abgenix and Medarex technologies.

Monoclonal antibodies are generally derived from non-human sources, rather than from human sources (Harlow and Lane (1988) Antibodies A Laboratory Manual, Cold Spring Harbor Laboratory, Cold Spring Harbor, N.Y., pp. 139-243). The use of non-human sources can limit the therapeutic efficiency of a monoclonal antibody. Antibodies derived from murine or other non-human sources can have the undesired properties of provoking an immune response, weak recruitment of effector function, and rapid clearance from the bloodstream (Baca, et al. (1997) J. Biol. Chem. 272:10678-10684). For these reasons, it may be desired to prepare therapeutic antibodies by humanization.

"Humanized antibody" means an antibody comprising an antigen-binding region of nonhuman origin, e.g., rodent, and at least a portion of an immunoglobin of human origin, e.g., a human framework region, a human constant region, or portion thereof (see, e.g., U.S. Pat. No. 6,352,832).

A humanized antibody contains the amino acid sequences from six complementarity determing regions (CDRs) of the parent mouse antibody, which are grafted on a human antibody framework. The content of non-human sequence in humanized antibodies is preferably low, i.e., about 5% (Baca, et al. (1997) J. Biol. Chem. 272:10678-10684). To achieve optimal binding, the humanized antibody may need fine-tuning, by changing certain framework amino acids, usually involved in supporting the conformation of the CDRs, back to the corresponding amino acid found in the parent mouse antibody. The framework amino acids that are generally changed back to those of the parent are those involved in supporting the conformation of the CDR loops (Chothia, et al. (1989) Nature 342:877-883; Foote and Winter (1992) J. Mol. Biol. 224:487-499). The framework residues that most often influence antigen binding is relatively small, and may be a small as eleven residues (Baca, et al. (1997) J. Biol. Chem. 272:10678-10684).

Humanized antibodies include antibodies having all types of constant regions, including IgM, IgG, IgD, IgA and IgE, and any isotype, including IgG1, IgG2, IgG3 and IgG4. When it is desired that the humanized antibody exhibit cytotoxic activity, the constant domain is usually a complement-fixing constant domain and the class is typically IgG1. When such cytotoxic activity is not desirable, the constant domain can be of the IgG2 class. The humanized antibody may comprise sequences from more than one class or isotype (U.S. Pat. No. 6,329,511 issued to Vasquez, et al.). The phage display technique can be used for screening for and selecting antibodies with high binding affinity (Hoogenboom and Chames (2000) Immunol. Today 21:371-377; Barbas, et al. (2001) Phage Display:A Laboratory Manual, Cold Spring Harbor Laboratory, Cold Spring Harbor, N.Y.; Kay, et al. (1996) Phage Display of Peptides and Proteins:A Laboratory Manual, Academic Press, San Diego, Calif.).

Antibodies can also be prepared or designed using the phage display method or human antibody libraries contained in transgenic mice (see, e.g., de Bruin, et al. (1999) Nature Biotechnology 17:397-399; Vaughan, et al. (1996) Nature Biotechnology 14:309-314; Barbas (1995) Nature Medicine 1:837-839; Mendez, et al. (1997) Nature Genetics 15:146-156; Huse, et al. (1989) Science 246:1275-1281; Ward, et al. (1989) Nature 341:544-546).

Antibodies are merely one form of specific binding compositions. Other binding compositions, which will often have similar uses, include molecules that bind with specificity to ligand or receptor, e.g., in a binding partner-binding partner fashion, an antibody-antigen interaction, or in a natural physiologically relevant protein-protein interaction, either covalent or non-covalent, e.g., proteins which specifically associate with desired protein. The molecule may be a polymer, or chemical reagent. A functional analog may be a protein with structural modifications, or may be a structurally unrelated molecule, e.g., which has a molecular shape which interacts with the appropriate binding determinants. Antibody binding compounds, including binding fragments, of this invention can have significant diagnostic or therapeutic value. They can be useful as non-neutralizing binding compounds and can be coupled to toxins or radionuclides so that when the binding compound binds to the antigen, a cell expressing it, e.g., on its surface, is killed. Further, these binding compounds can be conjugated to drugs or other therapeutic agents, either directly or indirectly by means of a linker, and may effect drug targeting.

Agonists include IL-27, conservatively modified variants or muteins thereof, fragments thereof, and chemical analogs. These polypeptides will be used to induce receptor signaling.

IV. Therapeutic Compositions; Diagnostics; Methods.

The present invention provides methods for using agonists of IL-27 and at least one other cytokine selected from IL-12, IL-2, IL-23, IL-15, and IL-18, for the treatment of, e.g., infections, including intracellular pathogens, cancers and tumors, cell proliferation, viral infections, inflammatory disorders, or autoimmune disorders.

Also provided are methods for using antagonists of antagonists of IL-27 and of at least one cytokine selected from IL-12, IL-2, IL-23, IL-15, and IL-18, for the treatment of, e.g., infections, including intracellular pathogens, cancers and tumors, cell proliferation, viral infections, inflammatory disorders, or autoimmune disorders.

The above methods using agonists are contemplated for the stimulation or enhancement of IFNgamma expression, e.g., for disorders treatable by IFNgamma, such tumors.

The above methods using antagonists are contemplated for the inhibition or reduction of IFNgamma expression or concentration, e.g., for treating TH1-type disorders or disorders associated with increased IFNgamma production, such as psoriasis, uveoretinitis, multiple sclerosis, Crohn's disease, systemic lupus erythematosus, lupus nephritis, Hashimoto's thyroiditis, and Graves' disease (see, e.g., Steinman (2001) *Curr. Opinion Immunol.* 13:597-600; Mizuguchi, et al. (2002) *Arch. Immunol. Ther. Exp.* (Warsz) 50:243-254; Rotondi, et al. (2003) *J. Endocrinol. Invest.* 26:177-180; Asadullah, et al. (1999) *Drugs Today (Barc)* 35:913-924; Ghoreschi, et al. (2003) *J. Mol. Med.* 81:471-480; Bouma and Strober (2003) *Nature Revs. Immunol.* 3:521-533; Tomita, et al. (2001) *J. Neurosci. Res.* 64:26-33; Richards, et al. (2001) *Kidney Int.* 60:2173-2180).

Also provided are methods for using the above agonists or antagonists for the treatment of autoimmune and inflammatory disorders, e.g., multiple sclerosis, fibrosis, rheumatoid arthritis, thyroiditis, lupus, psoriasis, diabetes, and inflammatory bowel disorder (IBD), including Crohn's disease, ulcerative colitis, and celiac disease.

Note that increased levels of IFNgamma are associated with protection or improvement in collagen-induced arthritis (CIA) and experimental autoimmune encephalitis (EAE), while decreased levels are associated with protection or improvement in experimental lupus and experimental diabetes, and that Crohn's disease is a TH1-type disease, associated with increased IFNgamma, while ulcerative colitis is a TH2-type disease.

Methods for using the above agonists or antagonists for the treatment of inflammatory or immune disorders of the lungs are provided, e.g., asthma, allergies, chronic obstructive pulmonary disorder (COPD), and idiopathic pulmonary fibrosis (see, e.g., Ikeda, et al. (2002) *Cytokine and Growth Factor Revs.* 13:95-109; Matthys, et al. (2000) *J. Leukocyte Biol.* 68:447-454; Younes and Amsden (2002) *J. Pharmaceutical Sci.* 91:2-17; Frucht, et al. (2001) *TRENDS Immunol.* 22:556-560; Bouma, supra; Klimp, et al. (2002) *Crit. Rev. Oncol. Hematol.* 44:143-161; Aggarwal and Behera (2000) *Expert Opin. Pharmacother.* 1: 1423-1427; Dorman and Holland (2000) *Cytokine Growth Factor Revs.* 11:321-333; Busse and Rosenwasser (2003) *J. Allergy Clin. Immunol.* 111:S799-S804; Skurkovich and Skurkovich (2003) Curr. Opin. Mol. Ther. 5:52-57).

The present invention provides methods to modulate activation, development, or proliferation of, e.g., T cells, monocytes/macrophages, NKT cells, NK cells, antigen presenting cells (APCs), including dendritic cells, B cells, neutrophils, and endothelial cells, including vascular endothelial cells. Also provided are methods to modulate expression of MHC Class I and MHC Class II, methods to modulate TH1-response, TH2-response, and methods to modulate IgE expression.

The antagonists and/or agonists of the present invention can be administered alone or in combination with another inhibitor or agonist of the same or accompanying pathway; or other compounds used for the treatment of symptoms, e.g., antagonists, or steroids such as glucocorticoids. Diagnostic methods include such aspects as prediction of prognosis; definition of subsets of patients who will either respond or not respond to a particular therapeutic course; diagnosis of immune or cancer related disorders or subtypes of these disorders; or assessing response to therapy.

Treatment, therapy, or diagnosis can be effected by direct administration of the agonist or antagonist or by administration of a nucleic acid encoding the agonist or antagonist. The agonist or antagonist encompasses a binding composition derived from an antibody, an antibody or antibody fragment that specifically binds IL-27 or an IL-27R, an IL-27 mutein or variant, an anti-sense nucleic acid, an interference RNA, or a vector expressing an nucleic acid encoding the agonist or antagonist (see, e.g., Arenz and Schepers (2003) *Naturwissenschaften* 90:345-359; Sazani and Kole (2003) *J. Clin. Invest.* 112:481-486; Pirollo, et al. (2003) *Pharmacol. Therapeutics* 99:55-77; Wang, et al. (2003) *Antisense Nucl. Acid Drug Devel.* 13:169-189).

To prepare pharmaceutical or sterile compositions including the antibody, binding composition thereof, cytokine agonist, or small molecule antagonist, the entity is admixed with a pharmaceutically acceptable carrier or excipient which is preferably inert. Preparation of such pharmaceutical compositions is known in the art, see, e.g., *Remington's Pharmaceutical Sciences and U.S. Pharmacopeia: National Formulary*, Mack Publishing Company, Easton, Pa. (1984).

Antibodies, binding compositions, or cytokines are normally administered parentally, preferably intravenously. Since such proteins or peptides may be immunogenic they are preferably administered slowly, either by a conventional IV administration set or from a subcutaneous depot, e.g., as taught by Tomasi, et al, U.S. Pat. No. 4,732,863. Methods to minimize immunological reactions may be applied. Small molecule entities may be orally active.

When administered parenterally the biologics will be formulated in a unit dosage injectable form (solution, suspension, emulsion) in association with a pharmaceutically acceptable parenteral vehicle. Such vehicles are typically inherently nontoxic and nontherapeutic. The therapeutic may be administered in aqueous vehicles such as water, saline, or buffered vehicles with or without various additives and/or diluting agents. Alternatively, a suspension, such as a zinc suspension, can be prepared to include the peptide. Such a suspension can be useful for subcutaneous (SQ) or intramuscular (IM) injection. The proportion of biologic and additive can be varied over a broad range so long as both are present in effective amounts. The antibody is preferably formulated in purified form substantially free of aggregates, other proteins, endotoxins, and the like, at concentrations of about 5 to 30 mg/ml, preferably 10 to 20 mg/ml. Preferably, the endotoxin levels are less than 2.5 EU/ml. See, e.g., Avis, et al. (eds.) (1993) *Pharmaceutical Dosage Forms: Parenteral Medications*, 2d ed., Dekker, NY; Lieberman, et al. (eds.) (1990) *Pharmaceutical Dosage Forms: Tablets*, 2d ed., Dekker, NY; Lieberman, et al. (eds.) (1990) *Pharmaceutical Dosage Forms: Disperse Systems*, Dekker, NY; Fodor, et al. (1991)

Science 251:767-773, Coligan (ed.) *Current Protocols in Immunology*; Hood, et al. (1984) *Immunology*, Pearson, Upper Saddle River, N.Y.; Paul (ed.) (1999) *Fundamental Immunology*, 4th ed., Lippincott Williams & Wilkins Publishers, Phila., PA; Parce, et al. (1989) *Science* 246:243-247; Owicki, et al. (1990) *Proc. Natl. Acad. Sci. USA* 87:4007-4011; and Blundell and Johnson (1976) *Protein Crystallography*, Academic Press, New York.

Selecting an administration regimen for a therapeutic depends on several factors, including the serum or tissue turnover rate of the entity, the level of symptoms, the immunogenicity of the entity, and the accessibility of the target cells, timing of administration, etc. Preferably, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate antibody doses is found in, e.g., Bach, et al., chapter 22, in Ferrone, et al. (eds.) (1985) *Handbook of Monoclonal Antibodies*, Noges Publications, Park Ridge, N.J.; and Haber, et al. (eds.) (1977) *Antibodies in Human Diagnosis and Therapy*, Raven Press, New York, N.Y. (Russell, pgs. 303-357, and Smith, et al., pgs. 365-389). Alternatively, doses of cytokine or small molecules are determined using standard methodologies.

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. Preferably, a biologic that will be used is derived from the same species as the animal targeted for treatment, thereby minimizing a humoral response to the reagent.

The total weekly dose ranges for antibodies or fragments thereof, which specifically bind to ligand or receptor range generally from about 10 µg, more generally from about 100 µg, typically from about 500 µg, more typically from about 1000 µg, preferably from about 5 mg, and more preferably from about 10 mg per kilogram body weight. Generally the range will be less than about 100 mg, preferably less than about 50 mg, and more preferably less than about 25 mg per kilogram body weight. Agonist or small molecule therapeutics may be used at similar molarities.

The weekly dose ranges for antagonists of cytokine receptor mediated signaling, e.g., antibody or binding fragments, range from about 1 µg, preferably at least about 5 µg, and more preferably at least about 10 µg per kilogram of body weight. Generally, the range will be less than about 1000 µg, preferably less than about 500 µg, and more preferably less than about 100 µg per kilogram of body weight. Dosages are on a schedule which effects the desired treatment and can be periodic over shorter or longer term. In general, ranges will be from at least about 10 µg to about 50 mg, preferably about 100 µg to about 10 mg per kilogram body weight. Cytokine agonists or small molecule therapeutics will typically be used at similar molar amounts, but because they likely have smaller molecular weights, will have lesser weight doses.

The present invention also provides for administration of biologics in combination with known therapies, e.g., vaccines, steroids, particularly glucocorticoids, which alleviate the symptoms, e.g., associated with inflammation, or antibiotics or anti-infectives. Daily dosages for glucocorticoids will range from at least about 1 mg, generally at least about 2 mg, and preferably at least about 5 mg per day. Generally, the dosage will be less than about 100 mg, typically less than about 50 mg, preferably less than about 20 mg, and more preferably at least about 10 mg per day. In general, the ranges will be from at least about 1 mg to about 100 mg, preferably from about 2 mg to 50 mg per day. The phrase "effective amount" means an amount sufficient to ameliorate a symptom or sign of the medical condition. Typical mammalian hosts will include mice, rats, cats, dogs, and primates, including humans. An effective amount for a particular patient may vary depending on factors such as the condition being treated, the overall health of the patient, the method route and dose of administration and the severity of side affects. When in combination, an effective amount is in ratio to a combination of components and the effect is not limited to individual components alone An effective amount of therapeutic will decrease the symptoms typically by at least about 10%; usually by at least about 20%; preferably at least about 30%; or more preferably at least about 50%. The present invention provides reagents which will find use in therapeutic applications as described elsewhere herein, e.g., in the general description for treating disorders associated with the indications described above. Berkow (ed.) *The Merck Manual of Diagnosis and Therapy*, Merck & Co., Rahway, N.J.; Brauwald, et al. (eds.) (2001) *Harrison's Principles of Internal Medicine*, 15th ed., McGraw-Hill, NY; Gilman, et al. (eds.) (1990) *Goodman and Gilman's: The Pharmacological Bases of Therapeutics*, 8th Ed., Pergamon Press; Remington's Pharmaceutical Sciences, 17th ed. (1990), Mack Publishing Co., Easton, Penn; Langer (1990) *Science* 249:1527-1533; *Merck Index*, Merck & Co., Rahway, N.J.; and Physician's Desk Reference (PDR); Cotran, et al. (eds.), supra; and Dale and Federman (eds.) (2000) *Scientific American Medicine*, Healtheon/WebMD, New York, N.Y.

The broad scope of this invention is best understood with reference to the following examples, which are not intended to limit the inventions to the specific embodiments.

EXAMPLES

I. General Methods.

Many of the standard methods below are described or referenced, e.g., in Maniatis, et al. (1982) *Molecular Cloning, A Laboratory Manual*, Cold Spring Harbor Laboratory, Cold Spring Harbor Press, NY; Sambrook, et al. (1989) *Molecular Cloning: A Laboratory Manual* (2d ed.) Vols. 1-3, CSH Press, NY; Ausubel, et al., *Biology*, Greene Publishing Associates, Brooklyn, N.Y.; or Ausubel, et al. (1987 and Supplements) *Current Protocols in Molecular Biology*, Wiley/Greene, NY; Inns, et al. (eds.) (1990) *PCR Protocols. A Guide to Methods and Applications*, Academic Press, NY. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification," *Methods in Enzymology*, vol. 182, and other volumes in this series; Coligan, et al. (1995 and supplements) *Current Protocols in Protein Science*, John Wiley and Sons, New York, N.Y.; P. Matsudaira (ed.) (1993) *A Practical Guide to Protein and Peptide Purification for Microsequencing*, Academic Press, San Diego, Calif.; and manufacturer's literature on use of protein purification products, e.g., Pharmacia, Piscataway, N.J., or Bio-Rad Laboratories, Hercules, Calif. Combination with recombinant techniques allow fusion to appropriate segments (epitope tags), e.g., to a FLAG sequence or an equivalent which can be fused, e.g., via a protease-removable sequence. See, e.g., Hochuli (1989) *Chemische Industrie* 12:69-70; Hochuli (1990) "Purification of Recombinant Proteins with Metal Chelate Absorbent" in Setlow (ed.) *Genetic Engineering, Principle and Methods* 12:87-98, Plenum Press, NY; and Crowe, et al. (1992) *QIAexpress. The High Level Expression & Protein Purification System*, QIAGEN, Inc., Chatsworth, Calif.

Standard immunological techniques are described, e.g., in Hertzenberg, et al. (eds.) (1996) *Weir's Handbook of Experimental Immunology* vols. 1-4, Blackwell, Malden, Mass.; Coligan (1991) *Current Protocols in Immunology* Wiley/Greene, NY; and *Methods in Enzymology* vols. 70, 73, 74, 84, 92, 93, 108, 116, 121, 132, 150, 162, and 163. Cytokine assays are described, e.g., in Thomson (ed.) (1998) *The Cytokine Handbook* (3d ed.) Academic Press, San Diego; Mire-Sluis and Thorpe (1998) *Cytokines*, Academic Press, San Diego, Calif.; Metcalf and Nicola (1995) *The Hematopoietic Colony Stimulating Factors*, Cambridge Univ. Press, Cambridge, UK; and Aggarwal and Gutterman (1991) *Human Cytokines*, Blackwell, Malden, Mass.

Assays for vascular biological activities are well known in the art. They will cover angiogenic and angiostatic activities in tumor, or other tissues, e.g., arterial smooth muscle proliferation (see, e.g., Koyoma, et al. (1996) *Cell* 87:1069-1078), monocyte adhesion to vascular epithelium (see, e.g., McEvoy, et al. (1997) *J. Exp. Med.* 185:2069-2077; Ross (1993) *Nature* 362:801-809; Rekhter and Gordon (1995) *Am. J. Pathol.* 147:668-677; Thyberg, et al. (1990) *Atherosclerosis* 10:966-990; Gumbiner (1996) *Cell* 84:345-357.

Assays for neural cell biological activities are described, e.g., in Wouterlood (ed. 1995) *Neuroscience Protocols modules* 10, Elsevier; *Methods in Neurosciences*, Academic Press; and *Neuromethods* Humana Press, Totowa, N.J. Methodology of developmental systems is described, e.g., in Meisami (ed.) *Handbook of Human Growth and Developmental Biology*, CRC Press; and Chrispeels (ed.) *Molecular Techniques and Approaches in Developmental Biology*, Interscience.

FACS analyses are described in Melamed, et al. (1990) *Flow Cytometry and Sorting*, Wiley-Liss, Inc., New York, N.Y.; Shapiro (1988) *Practical Flow Cytometry*, Liss, New York, N.Y.; and Robinson, et al. (1993) *Handbook of Flow Cytometry Methods*, Wiley-Liss, New York, N.Y.

II. Induction of IFNgamma.

The ability of human IL-27 and mouse IL-27 to induce the production of IFNgamma in the presence of a neutralizing anti-IL-2 mAb, was measured, with costimulation via anti-CD3 or with anti-CD3/anti-CD28. Cells were treated in the absence and presence of IL-12.

In tests of human CD4$^+$CD45RA T cells, neither hIL-27 nor hIL-12 by itself induced IFNgamma production, where cells were also treated with anti-CD3 or with anti-CD3/anti-CD28. Only in the presence of both IL-27 and IL-12 was there detectable IFNgamma production, demonstrating a strong synergy between IL-27 and IL-12.

Tests of sorted mouse CD4$^+$CD45RB$^{high}$ naïve T cells also demonstrated synergy between IL-27 and IL-12. Sorted mouse CD4$^+$CD45RB$^{high}$ naïve T cells were stimulated for 4 days with anti-CD3 mAb alone or with anti-CD3 mAb/anti-CD28 mAb and saturating amounts of IL-27 and/or IL-12. With anti-CD3 only (no anti-CD28 stimulation) neither IL-27 nor IL-12 by itself was capable of inducing substantial amounts of IFNgamma. However, the combination of IL-27 and IL-12 induced up to about 300 ng/ml of IFNgamma. With anti-CD3/anti-CD28 co-stimulation, IL-27 alone as well as IL-12 alone was capable of inducing IFNgamma production. The combination of both IL-27 and IL-12 led to an additive effect with IFNgamma produced at levels up to about 550 ng/ml.

The study of the present invention has examined the effects of IL-27 on the production of IFNgamma by natural killer (NK) cells. Human CD56 positive NK cells were isolated from peripheral blood mononuclear cells of normal healthy donors using positive adherence selection with anti-CD56 coated microbeads (Miltenye, Auburn, Calif.), followed by positive sorting of CD56$^+$CD3$^-$ cells. The NK cells thus isolated were then cultured in the presence of a cytokine, or a cytokine combination, for 72 hours at 37° C. Cell culture supernatants were harvested and the amounts of IFNgamma in the supernatants were determined by ELISA. In addition, RNA was isolated from cell pellets and analyzed for expression of IFNgamma mRNA.

A typical set of results is shown (Table 1).

TABLE 1

The effect of IL-27 on production of IFNgamma (ng/ml) from NK cells. IL-2 (200 units/ml), IL-12 (1.0 ng/ml), and IL-18 (0.1 mg/ml), were added at the indicated concentrations.

| Concentration of IL-27 added (ng/ml). | +IL-12 | +IL-2 and IL-12 | +IL-2 and IL-18 | +IL-2, IL-12, and IL-18 |
|---|---|---|---|---|
| | | IFNgamma produced (ng/ml) | | |
| 100 | 3 | 50 | 52 | 1831 |
| 20 | 0.4 | 39 | 47 | 1082 |
| 4 | 0.2 | 25 | 19 | 476 |
| 0.8 | 0.2 | 16 | 15 | 168 |
| 0.16 | 0.2 | 3 | 9.7 | 136 |
| 0 | 0.2 | 1.2 | 2.1 | 52 |

The concentration of IL-27 (ng/ml) used in each experiment is indicated (leftmost column, Table 1). The data represent the amount of IFNgamma (ng) produced. Thus, IL-12 alone induced IFNgamma production by purified NK cells at a low level (less than 1 ng/ml). IL-27 alone did not induce detectable IFNgamma production (data not shown). Addition of IL-27 to IL-12, however, enhanced the production of IFNgamma by 10-20 fold, i.e., to about 3.0 ng/ml. Therefore, IL-27 acted synergistically with IL-12 to enhance IFNgamma production.

IL-27 also has a synergistic effect on other cytokines or cytokine combinations. The combination of IL-12 and IL-2, in the absence of IL-27, resulted in increased production of IFNgamma compared to IL-12 alone. Again, addition of IL-27 to the combination of IL-2 and IL-12 led to a dose-dependent increase in the level of IFNgamma (up to 50-100 ng/ml). The most striking synergistic effect was observed when IL-2, IL-12 and IL-18 were combined with IL-27. The triple combination, in the absence of IL-27, resulted in IFNgamma production levels of 50-100 ng/ml. Addition of IL-27 to the triple combination resulted in a dose dependent synergistic production of IFNgamma up to about 2000 ng/ml (Table 1). In similar studies, it was shown that IL-15 can be used in place of IL-2, while IL-23 can be used in place of IL-12.

Interestingly, mRNA analysis using real time polymerase chain reaction indicates that the synergistic effect of IL-27 and other cytokines is not reflected by an increase in the amount of IFNgamma mRNA (Table 2). Therefore, the enhancement of production is likely exerted at the translational or post-translational level.

The results demonstrate that saturating amounts of previously characterized cytokine combinations do not produce levels of IFNgamma production that can be achieved with the addition of IL-27. Therefore, production of IFNgamma to its full potential is dependent on the presence of a select set of cytokines, and omitting one of them can create a rate-limiting effect.

TABLE 2

Relative expression of interferon-gamma from human NK cells, as determined by Taqman ® real time PCR.

| Condition | Relative expression | Condition | Relative expression |
|---|---|---|---|
| NK media only | 1 | IL-2 + IL-12 | 2800 |
| 1:625 IL-27 | 1 | IL-27 + 1:625 IL-2 + IL-12 | 1500 |
| 1:125 IL-27 | 1 | IL-27 + 1:125 IL-2 + IL-12 | 1600 |
| 1:25 IL-27 | 1 | IL-27 + 1:25 IL-2 + IL-12 | 1700 |
| 1:5 IL-27 | 1 | IL-27 + 1:5 IL-2 + IL-12 | 2600 |
| 100 ng/ml IL-27 | 1 | IL-27 + IL-2 (100 ng/ml) + IL-12 | 2100 |
| IL-2 only (100 ng/ml) | 320 | IL-2 + IL-18 | 500 |
| IL-27 + 1:625 IL-2 | 120 | IL-27 + 1:625 IL-2 + IL-18 | 300 |
| IL-27 + 1:125 IL-2 | 240 | IL-27 + 1:125 IL-2 + IL-18 | 300 |
| IL-27 + 1:25 IL-2 | 340 | IL-27 + 1:25 IL-2 + IL-18 | 600 |
| IL-27 + 1:5 IL-2 | 310 | IL-27 + 1:5 IL-2 + IL-18 | 500 |
| IL-27 + IL-2 (100 ng/ml) | 190 | IL-27 + IL-2 (100 ng/ml) + IL-18 | 600 |
| IL-12 only (100 ng/ml) | 650 | IL-2 + IL-12 + IL-18 | 7600 |
| IL-27 + 1:625 IL-12 | 740 | IL-27 + 1:625 IL-2 + IL-12 + IL-18 | 6100 |
| IL-27 + 1:125 IL-12 | 710 | IL-27 + 1:125 IL-2 + IL-12 + IL-18 | 6800 |
| IL-27 + 1:25 IL-12 | 690 | IL-27 + 1:25 IL-2 + IL-12 + IL-18 | 6100 |
| IL-27 + 1:5 IL-12 | 705 | IL-27 + 1:5 IL-2 + IL-12 + IL-18 | 7000 |
| IL-27 + IL-12 (100 ng/ml) | 820 | IL-27 + IL-2 (100 ng/ml) + IL-12 + IL-18 | 4900 |
| IL-18 only | 1 | IL-2 only | 100 |
| IL-27 + 1:625 IL-18 | 1 | IL-12 + 1:625 IL-2 | 800 |
| IL-27 + 1:125 IL-18 | 1 | IL-12 + 1:125 IL-2 | 1700 |
| IL-27 + 1:25 IL-18 | 1 | IL-12 + 1:25 IL-2 | 2300 |
| IL-27 + 1:5 IL-18 | 1 | IL-12 + 1:5 IL-2 | 1800 |
| IL-27 + IL-18 (100 ng/ml) | 1 | IL-12 + IL-2 (10 ng/ml) | 2100 |

III. IL-27 Does Not Drive Th2 Polarization of Naïve T Cells.

Sorted mouse CD4+CD45RB$^{high}$ T cells were cultured with plate bound anti-CD3 and anti-CD28 in the presence of IL-4 and IL-27. Including IL-27 in the cultures led to a decreased IL-13 production both in the absence and presence of IL-4. Thus, while inducing a strong Th1 response, IL-27 does not appear to promote Th2 polarization.

IV. IL-27 Binds to WSX-1/TCCR.

Because of the relationship between IL-27 and the IL-6/IL-12 family, the search for the signaling receptors was concentrated on this family. Members of this family were introduced into BaF3 cells and tested for binding to IL-27. Of the receptors tested only Ba/F3 cells expressing the orphan cytokine receptor WSX-1/TCCR showed binding to tagged IL-27 (see, e.g., Sprecher, et al. (1998) *Biochem. Biophys, Res. Comm.* 246:82-90; Chen, et al. (2000) *Nature* 407:916-920). BaF3 cells infected with retroviral constructs expressing either F-tagged human or mouse WSX-1 cDNA (F-hWSX-1 or F-mWSX-1) showed cellular staining using anti-Flag mAb. Cells expressing F-hWSX-1 were then incubated with either hEBI3-Ig alone or with coexpressed hp28-E and EBI3-Ig for two hours. Heterodimeric p28/EBI3 bound to WSX-1 while EBI3-Ig itself showed no detectable binding. Similarly, only the combination of mp28-E and mEBI3-Ig provided a detectable interaction with mWSX-1-expressing BaF3 cells, whereas the two individual proteins were not able to do so. Incubation of independently expressed mp28-E and mEBI3-Ig with F-mWSX-1 expressing BaF3 cells also led to cellular staining. Untransfected control cells were not stained by p28/EBI3, demonstrating the specificity of the observed interactions.

These results were confirmed by co-immunoprecipitation experiments using a soluble extracellular form of hWSX-1 with a C-terminal RSGH$_6$-tag (R). Proteins from supernatants of transiently transfected HEK293T cells containing F-hEBI3 or coexpressed hp28-E/F-hEBI3 were immunoprecipitated using either Flag M2-agarose, protein G Sepharose®-coupled anti-etag mAb or protein G Sepharose®-coupled anti-H$_5$ mAb. The primary precipitates were washed and then incubated with HEK293T cell supernatants containing shWSX-1-R. Secondary precipitates were separated by SDS-PAGE and subjected to western blot. Precipitated proteins were visualized by ECL using antibodies against the respective protein tags. Only when all three proteins were present (h-p28-E, F-hEBI3 and shWSX-1-R), immunoprecipitation of one protein brought down both other components independently of the immunoprecipitating antibody used. The same co-immunoprecipitation experiment using the respective mouse orthologues had similar results.

To address the question if WSX-1 was sufficient to mediate IL-27 signal transduction, proliferation of BaF3 cells expressing human or mouse WSX-1 was tested. These cells proliferate in response to IL-3 but did not proliferate in response to IL-27. Thus WSX-1 appears to be required but not sufficient for IL-27 mediated signal transduction. The identification of additional IL-27 signal transducing receptor subunits is currently in progress.

All references cited herein are incorporated herein by reference to the same extent as if each individual publication, patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method of inhibiting IFNγ production from a cell, comprising contacting the cell with an effective amount of a first antibody or antibody fragment thereof that antagonizes IL-27 activity in conjunction with an effective amount of a second antibody or antibody fragment that inhibits activity of IL-12.

2. The method of claim 1 wherein the cell is a human cell selected from the group consisting of an NK cell and a T cell.

3. The method of claim 1, wherein the first antibody or antibody fragment thereof binds to a polypeptide selected from the group consisting of p28, EBI3, a complex of p28 and EBI3, and WSX-1/TCCR.

4. The method of claim 3, wherein the first antibody or antibody fragment thereof binds the polypeptide with a $K_D$ of at least $10^{-3}$ M.

5. The method of claim 3, wherein the first antibody or antibody fragment thereof binds the polypeptide with a $K_D$ of at least $10^{-6}$ M.

6. The method of claim 3, wherein the first antibody or antibody fragment thereof binds the polypeptide with a $K_D$ of at least $10^{-11}$ M.

7. The method of claim 1 wherein the first and second antibody or antibody fragment thereof are humanized or chimeric.

* * * * *